(12) United States Patent
Young

(10) Patent No.: US 6,502,579 B2
(45) Date of Patent: Jan. 7, 2003

(54) LASER ONYCHECTOMY BY RESECTION OF THE REDUNDANT EPITHELIUM OF THE UNGUAL CREST

(76) Inventor: William P. Young, 5860 Waterloo Rd., Canal Winchester, OH (US) 43110

(*) Notice: Subject to any disclaimer, the term of this patent is extended or adjusted under 35 U.S.C. 154(b) by 18 days.

(21) Appl. No.: 09/761,993

(22) Filed: Jan. 17, 2001

(65) Prior Publication Data

US 2001/0034515 A1 Oct. 25, 2001

Related U.S. Application Data

(60) Provisional application No. 60/176,965, filed on Jan. 19, 2000.

(51) Int. Cl.[7] .......................... A61B 19/00; B66F 15/00
(52) U.S. Cl. .......................... 128/898; 606/9; 606/127; 254/18
(58) Field of Search .................. 606/8, 9, 127, 606/131; 128/898; 254/18, 25; 132/73

(56) References Cited

U.S. PATENT DOCUMENTS

| | | | | |
|---|---|---|---|---|
| 4,767,333 A | * | 8/1988 | Born | 434/262 |
| 5,060,678 A | * | 10/1991 | Bauman | 132/732 |
| 5,782,249 A | * | 7/1998 | Weber et al. | 132/200 |
| 6,060,461 A | * | 5/2000 | Drake | 514/54 |
| 6,165,170 A | * | 12/2000 | Wynne et al. | 606/9 |

OTHER PUBLICATIONS

Douglas H. Slatter, B.V.Sc., M.S., Ph.D., F.R.C.V.S., Textbook of Small Animal Surgery, 1985, vol. 1, pp. 509–510, W.B. Saunders Company, Philadelphia, PA.

* cited by examiner

*Primary Examiner*—Michael Peffley
*Assistant Examiner*—Ahmed M. Farah
(74) *Attorney, Agent, or Firm*—Jason H. Foster; Kremblas, Foster, Phillips & Pollick

(57) ABSTRACT

A surgical process for removing the third phalanx of a feline, and most commonly a housecat, while reducing bleeding, swelling, pain and tissue deficit. A circumferential incision is formed on the epidermis of the ungual crest and traction is applied to the epidermis in a cranial direction. This exposes the extensor tendon and synovium, which are incised by the laser from a dorsal position aimed in a palmar direction. While applying traction to the third phalanx in a palmar direction, the collateral ligaments are ablated, permitting further disarticulation of the PII–PIII joint. Finally, the flexor tendon and tissue of the pad are incised by the laser from a dorsal position, permitting removal of the third phalanx. The declaw site is then covered with the redundant epithelium preserved in this process.

6 Claims, 21 Drawing Sheets

(17 of 21 Drawing Sheet(s) Filed in Color)

LASER ONYCHECTOMY BY RESECTION OF THE REDUNDANT EPITHELIUM OF THE UNGUAL CREST

This appln claims benefit of Prov. No. 60/176,965 filed Jan. 19, 2000.

BACKGROUND OF THE INVENTION

1. Field of the Invention

This invention relates generally to animal surgical procedures, and more particularly to a process for removing one or more claws of domesticated cats.

2. Description of the Related Art

For the purpose of medical necessity, due to trauma or infection, or because of owner election, the claws of felines, and most commonly household cats, are frequently removed. It is the second most performed elective procedure next to sterilization and practiced by veterinarians worldwide.

Onychectomy is the disarticulation and removal of the third phalanx in cats. Conventionally, onychectomy has been performed using mechanical cutting instruments, such as scalpels and clippers, to sever the skin, ligaments, tendons, and synovium at the PII–PIII joint. The instruments mechanically sever all of the tissue along a transverse plane passing between the second and third phalanges (PII–PIII) in the manner of a guillotine. Conventional onychectomy procedures cause complications due to the nature of the instruments used. The complications are hemorrhage, pain, swelling and tissue deficit due to removal of PIII. The tissue deficit is generally closed with sutures or tissue adhesives.

The complications of hemorrhage, pain and swelling have been reduced with the introduction of the $CO_2$ surgical laser. Exposure of the laser beam to tissue excites water molecules within tissue cells. The energy of the laser vaporizes the water in the cells and thereby ruptures the cells. The laser causes minimal damage to adjacent cells due to the fact that the beam is so narrow. Vaporization of cells coagulates small blood vessels and resects nerves with minimal trauma.

Although laser onychectomy reduces hemorrhaging, pain and swelling, traditional laser techniques retain the guillotine-oriented cutting path, thereby resulting in tissue deficit at the site where the third phalanx is removed. This deficit necessitates epidermal closure to cover the surgical site. As previously stated, this involves suturing the epidermis or closing it with tissue adhesive. Frequently no closure is used and the deficit closes by secondary intention resulting in delayed healing and the increased possibility of infection.

BRIEF SUMMARY OF THE INVENTION

The invention is a feline onychectomy surgical method using a laser cutting instrument. The method removes the third phalanx with reduced bleeding, pain and swelling by strict anatomical dissection of only connective tissue structures. Most importantly, the technique leaves a substantial portion of tissue to cover the exposed tip of the second phalanx. This eliminates the need for surgical closure of the remaining epidermis and decreases the incidence of infection.

The method includes forming a first circumferential incision with the laser in the epidermis at the edge of the ungual crest of the feline's claw. This first incision severs the most distal portion of the epidermis from the underlying fascia of the ungual crest. After the first incision, the surgeon applies cranial traction to the epidermis severed from the ungual crest to displace the distal edge of the epidermis cranially.

A second circumferential incision is preferably formed in the epidermis about 3 millimeters cranial to the first circumferential incision. This distance can vary, depending upon the size of the feline, but 3 millimeters is common for the domesticated cat. This second incision extends deeper into the subcutaneous fascia and further facilitates the cranial displacement of the epidermis from the ungual crest.

After making the second incision, the epidermis is pushed cranially and the extensor tendon is incised near its insertion on the ungual crest. This incision is formed by directing the laser beam in a substantially palmar direction when a laser beam source is positioned substantially dorsally of the extensor tendon. Next, the synovium of the PII–PIII joint is incised and traction is applied to the claw in the palmar direction to begin to disarticulate the PII–PIII joint and allow access to the medial and lateral collateral ligaments.

The medial and lateral collateral ligaments are ablated by directing the laser beam in a substantially palmar direction when the laser source is positioned substantially dorsally of the ligaments. This allows further disarticulation of the PII–PIII joint and access to the digital flexor tendon by palmar rotation of PIII. Next, the digital flexor tendon is incised by directing the laser beam in a substantially palmar direction when the laser source is positioned substantially dorsally of the flexor tendon. This allows for extreme palmar rotation of PIII and reveals the subcutaneous tissues of the pad.

Finally, the subcutaneous tissues of the pad of the second phalanx are incised by directing the laser beam in a substantially palmar direction when the laser source is positioned substantially dorsally of the subcutaneous tissues of the pad of the second phalanx.

The invention involves resection of the redundant epidermis to allow complete anatomical dissection and removal of the claw from a strictly cranio-dorsal approach. By operating only from the dorsal part of the paw and anatomically dissecting PIII by vaporizing only the connective tissue structures, trauma to the surrounding tissue is minimized. The preserved epidermis of the ungual crest that is normally discarded by all other techniques is retained to cover virtually all of the surgical site.

Of course, this surgical process will be recognized by a person having ordinary skill in the art to be adaptable to other animals, specifically dogs.

BRIEF DESCRIPTION OF THE SEVERAL VIEWS OF THE DRAWINGS

The file of this patent containg at least one drawing executed in color.

Figure 1:
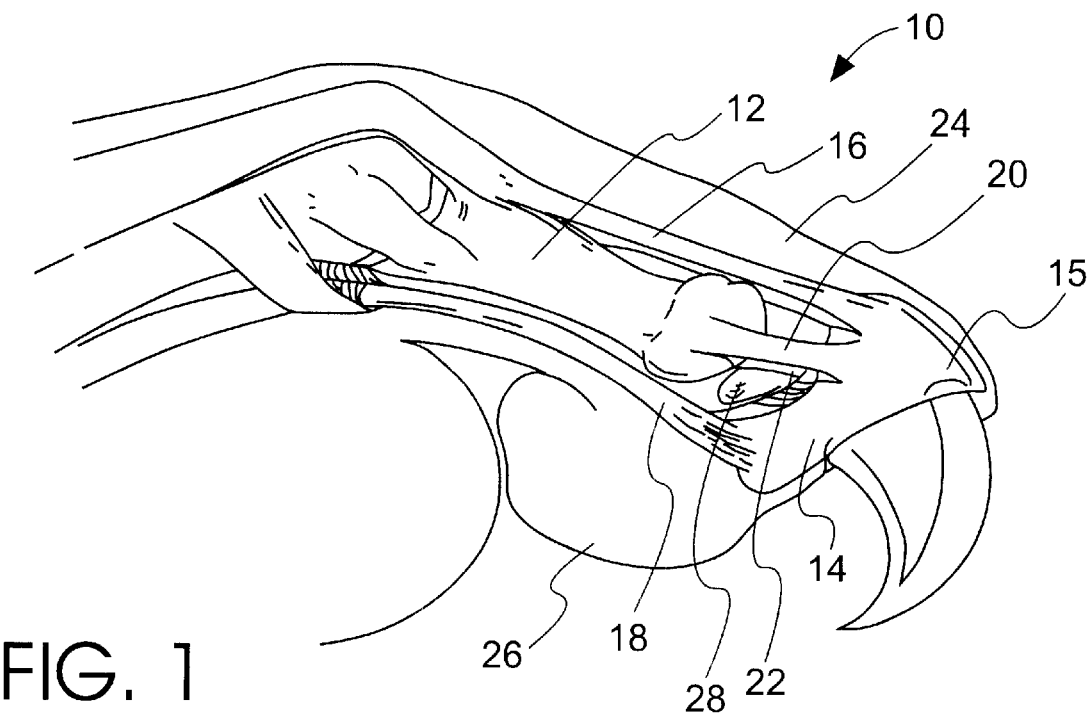
FIG. 1 is a schematic side view illustrating the normal digit of the domesticated cat.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or term similar thereto are often used. They are not limited to direct connection, but include connection through other elements where such connection is recognized as being equivalent by those skilled in the art.

DETAILED DESCRIPTION OF THE INVENTION

The process of the present invention proceeds as illustrated in the Figures. FIG. 1 shows a feline appendage 10, including the second phalanx 12 and the third phalanx 14 with the ungual crest 15. The phalanges 12 and 14 are connected by the extensor tendon 16, the flexor tendon 18, the collateral ligaments 20 and 22, the epithelium 24 and the pad 26. The synovium 28 is positioned in the joint between the second and third phalanges 12 and 14. It also connects the phalanges together.

A preliminary step to this procedure is the cleaning of the area to be operated upon. The patient should be premedicated and anesthetized in accordance with aseptic surgical protocol. The hair need not be clipped because the area is normally devoid of hair. The patient is prepped in lateral recumbancy and draped. A forcep is placed upon the claw that is to be removed.

There are four major steps to the process. They are (1) resection of the redundant tissue of the ungual crest; (2) incision of the extensor tendon and the synovium; (3) ablation of the collateral ligaments; and (4) incision of the flexor tendon and dissection of the subcutaneous tissue of the pad. These steps are described below in the preferred order in which they are taken.

The preferred method includes the positioning of the laser source dorsally of the paw and pointed in a palmar direction. All incisions are made with a laser, such as a $CO_2$ laser set at 4 to 6 watts, and preferably a continuous wave form. The laser source is commonly an elongated handpiece but could include any structure from which the beam is directed just prior to striking tissue. The laser source is positioned in a substantially dorsal position and pointed in a palmar direction. It will be apparent that momentary movement of the laser source from the dorsal position may be necessary during cutting to avoid directing the beam onto tissue that should not be cut. However, all contemplated applications of the laser's beam are in a palmar direction from a dorsal position.

Figure 2:
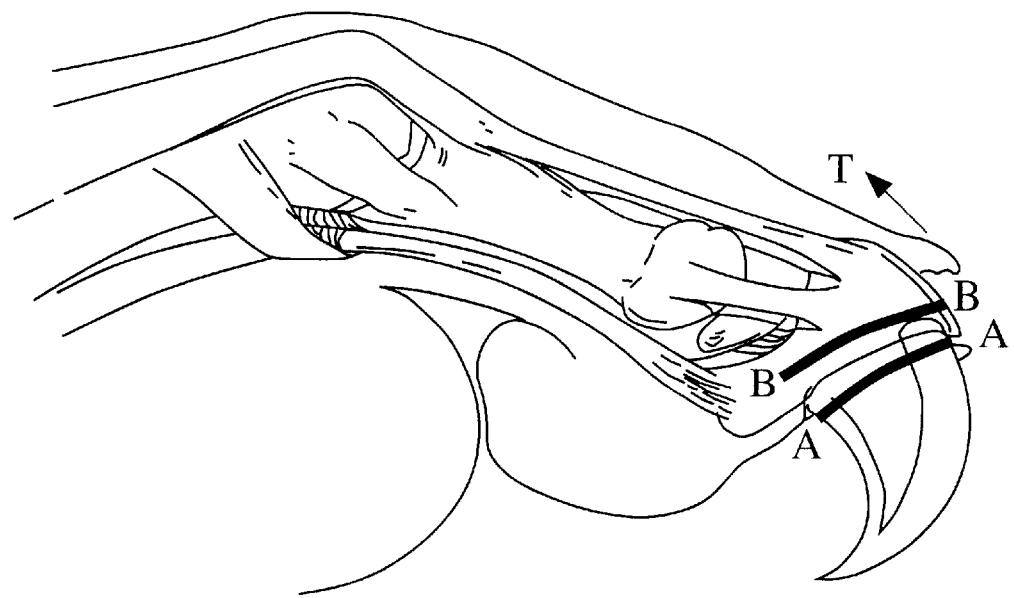
FIG. 2 is a schematic illustration of the first and second circumferential incisions of the epidermis of the ungual crest.

The first major step in the process is the formation of an incision in the redundant epidermis of the ungual crest 15 of the claw along the line A—A of FIG. 2. This incision is made near the most distal edge of the epidermis and extends circumferentially around the claw to sever the epidermis from the ungual crest 15. The distal edge of the severed epidermis is moved cranially by gentle traction applied in the direction of the arrow, T.

The traction in the direction T causes the epithelium to release from its distal attachment and permits a second circumferential incision of the redundant epithelium approximately 3 millimeters cranial from the first incision along the line B—B. This second incision allows slightly deeper subcutaneous fascia to be moved cranially over the ungual crest as well.

The tissue pushed cranially will later form a covering for the opening formed by the removal of the claw. This thereby avoids the problem of tissue deficit inherent in all known onychectomy procedures.

The position of the second incision 3 millimeters cranial of the first incision is based upon the average size of the household cat. For smaller animals the distance will be smaller, and for larger animals the distance will be larger.

Figure 3:
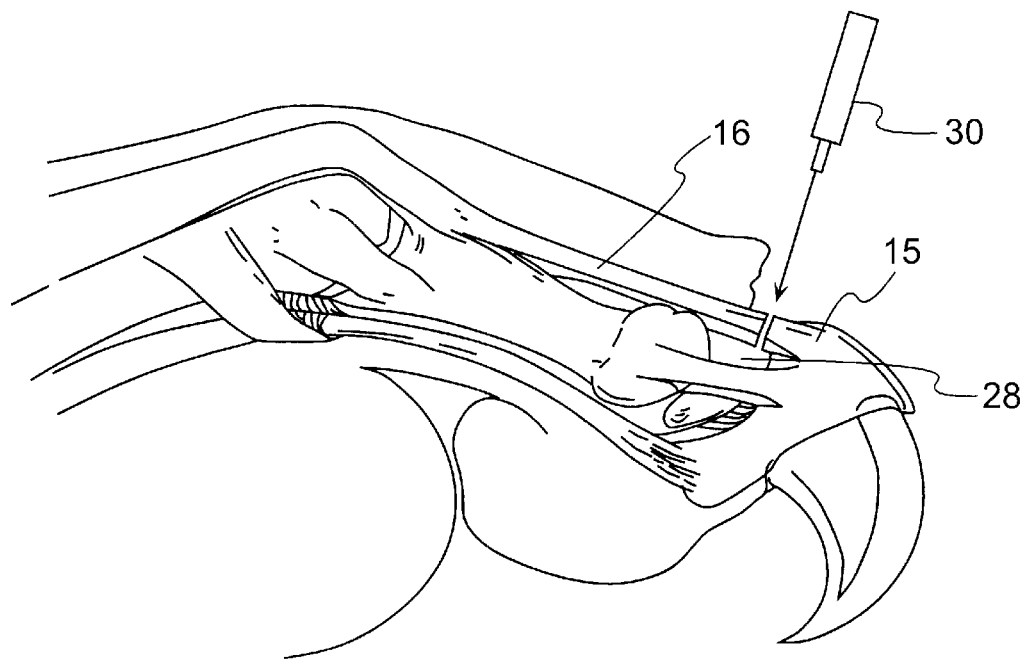
FIG. 3 is a schematic illustration of the incision of the digital extensor tendon side view.

Once the epidermis is pushed cranially, the second major step of the process can be taken. In the second step, as shown in FIG. 3, the extensor tendon 16 is resected at its insertion on the ungual crest 15 by the dorsally-positioned laser source 30 pointed in a palmar direction. The redundant epithelium is kept pushed cranially over the ungual crest and the laser completely severs the tendon 16 from the ungual crest.

Once the extensor tendon 16 is severed, traction is applied to the claw in a palmar direction by the forcep, causing the joint to become distracted. Care is taken to avoid applying too much traction, which will cause bleeding due to the tissue tearing rather than being incised. In the same step, using a slightly extended incision, the synovium 28 of PII–PIII is incised. Further traction applied to the claw in a palmar direction will permit further disarticulation of the joint as shown in FIG. 4, thereby exposing the collateral ligaments 20 and 22.

Figure 4:
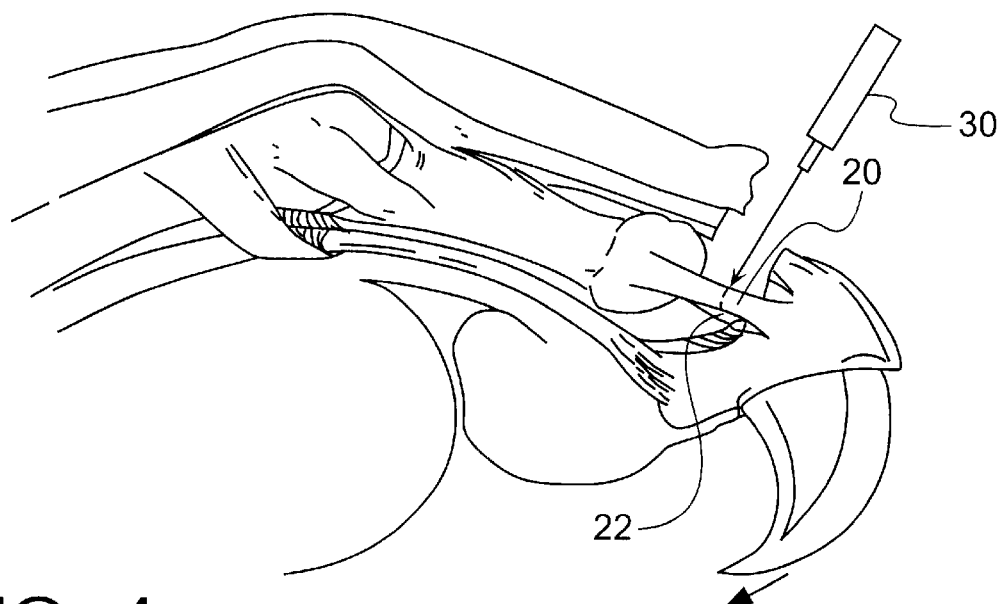
FIG. 4 is a schematic illustration of incision of the joint capsule of PII–PIII, palmar disarticulation, and direction of the ablation of the collateral ligaments.

The third major step, as shown in FIG. 4, is to ablate the medial and lateral collateral ligaments 20 and 22. The laser source 30 in the dorsal position of the limb 10 is directed in a palmar direction onto the ligaments 20 and 22 in a direct "head on" fashion. The ligaments 20 and 22 are vaporized until they are completely severed. Gentle traction in a palmar direction is applied to disarticulate the PII–PIII joint even further to the position shown in FIG. 5.

Figure 5:
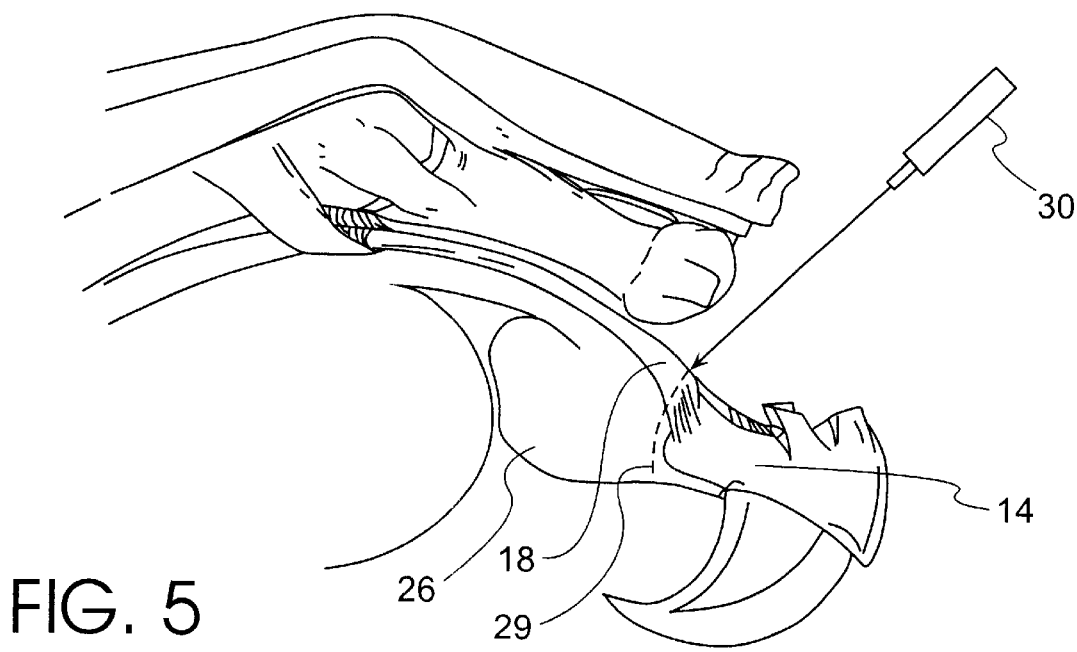
FIG. 5 is a schematic side view illustrating the palmar disarticulation of PIII and the incision of the digital flexor tendon. It also illustrates the plane of dissection of the subcutaneous tissues from the pad of PII.
Figure 6:
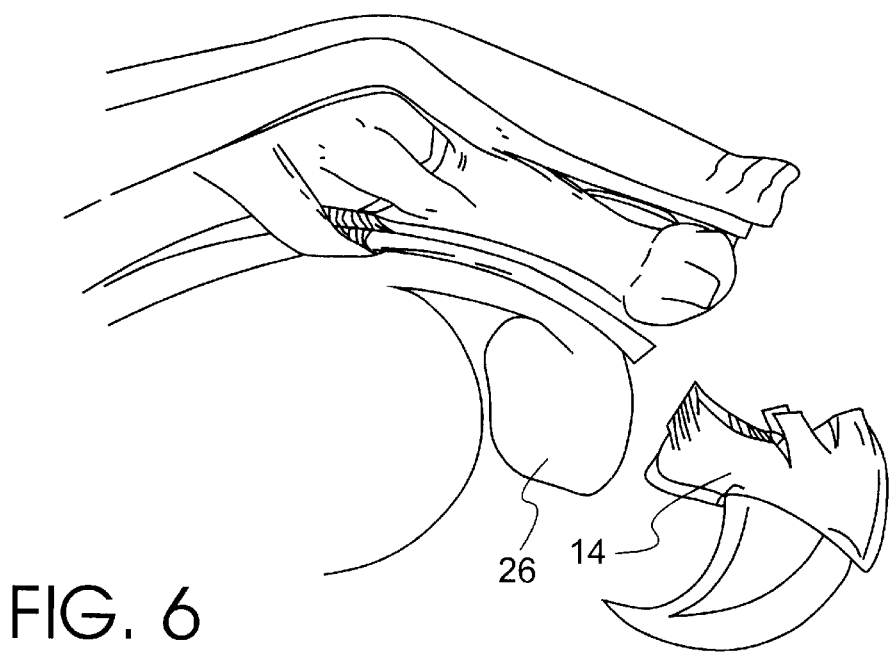
FIG. 6 is a schematic side view illustrating the claw after it has been removed from the second phalanx.

The fourth major step is the incision of the digital flexor tendon 18 and the dissection of the subcutaneous tissues of the pad 28 along the line 29 from the third phalanx 14. The third phalanx 14 is rotated in an extreme palmar direction, making the flexor tendon 18 visible and accessible to the laser's beam from a dorsal position. The laser is pointed in a palmar direction, and as the flexor tendon 18 is vaporized, traction in a palmar direction causes continued disarticulation as shown in FIG. 5. Once the flexor tendon 18 is completely severed, the subcutaneous tissue of the pad 28 of the third phalanx 14 is dissected as shown in FIG. 6.

During the fourth major step, the palmar surface of the third phalanx is exposed dorsally due to the extreme palmar rotation, permitting palmar attachments of the subcutaneous tissue to be incised from a dorsal position. This allows for easy dissection by continued palmar rotation. The laser beam is kept close to the surface of the third phalanx 14 to prevent any significant damage to the redundant epithelium.

Figure 7:
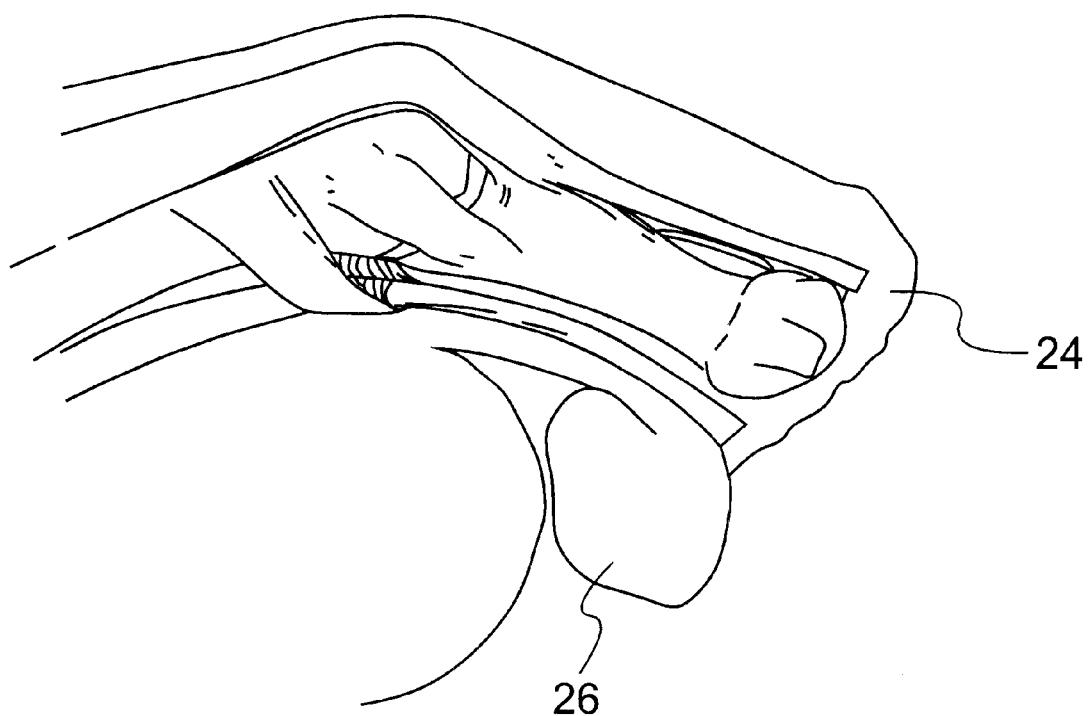
FIG. 7 is a schematic side view illustrating the remaining portion of the cat's appendage with the redundant epithelium pushed back over the declaw site.
Figure 8:
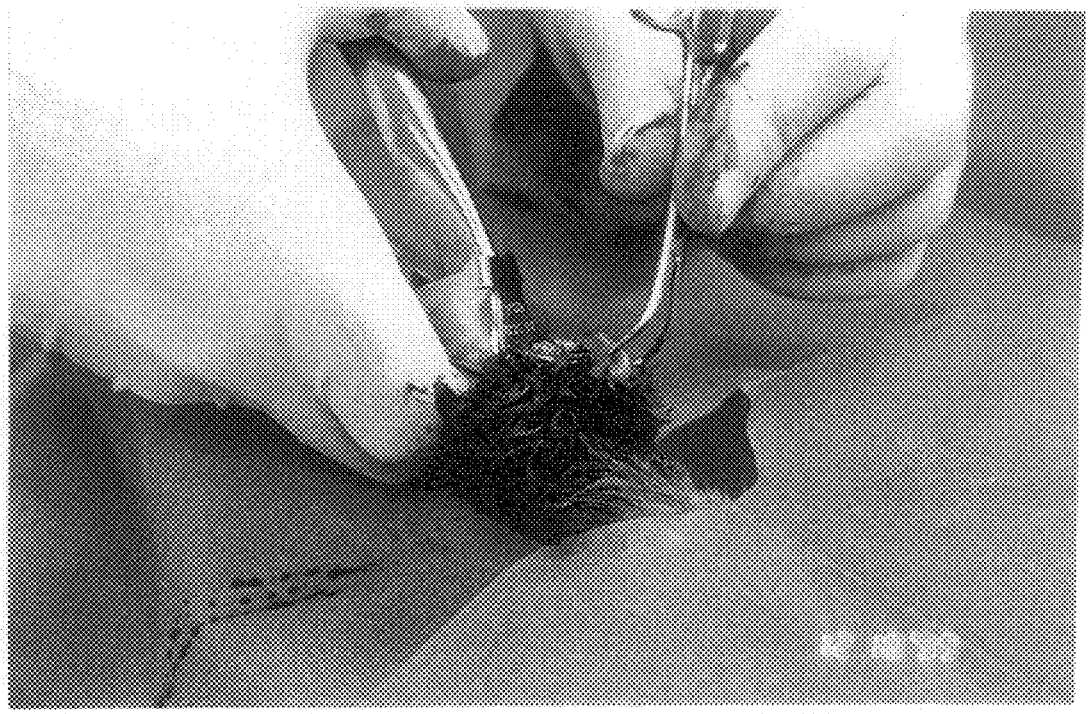
FIG. 8 is a photographic illustration of a prior art onychectomy process utilizing a guillotine method of onychectomy by utilization of Resco nail trimmers.
Figure 9:
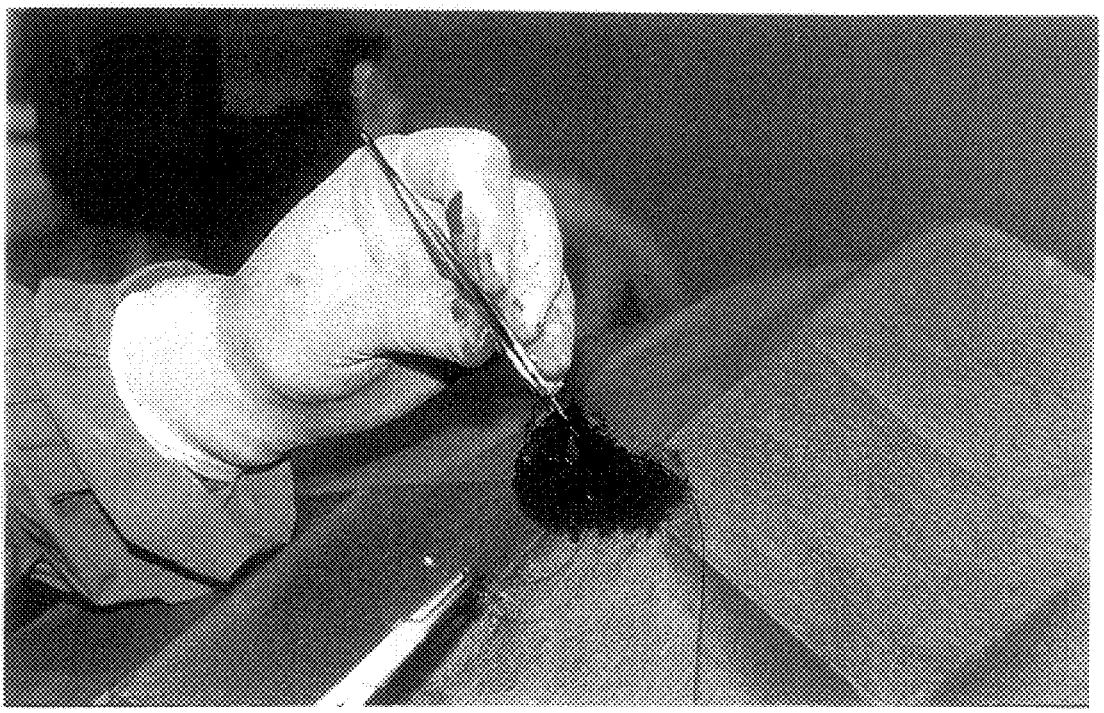
FIG. 9 is a photographic illustration of a prior art onychectomy process involving closure of the epidermis after the mechanical declaw of FIG. 8.
Figure 10:
FIG. 10 is a photographic illustration of the claw after the first circumferential incision in the epidermis at the edge of the ungual crest.
Figure 11:
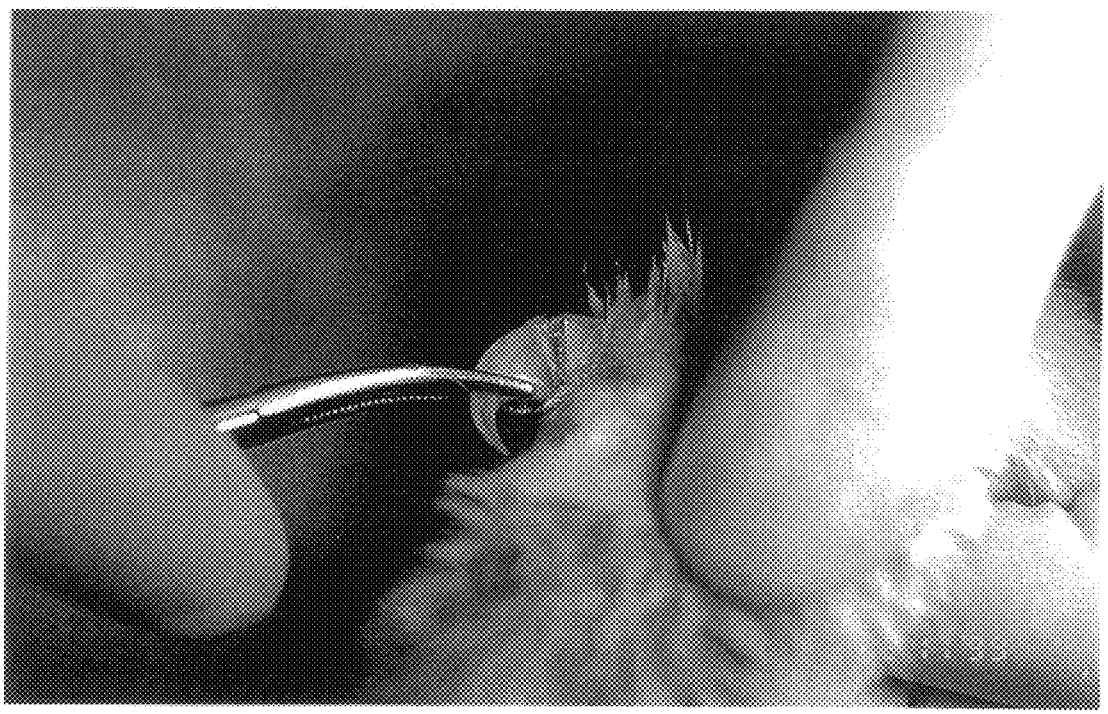
FIG. 11 is a photographic illustration of the claw after the first circumferential incision in the epidermis at the edge of the ungual crest.
Figure 12:
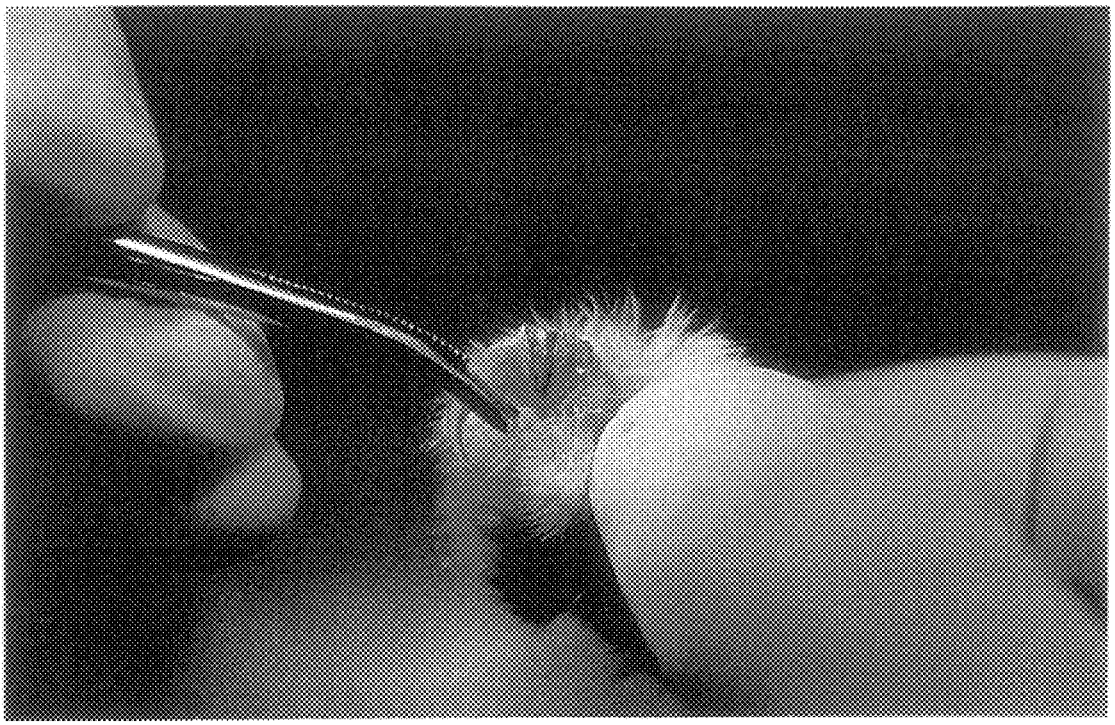
FIG. 12 is a photographic illustration of the claw after the second circumferential incision in the epidermis about 3 millimeters cranial to the first circumferential incision.
Figure 13:
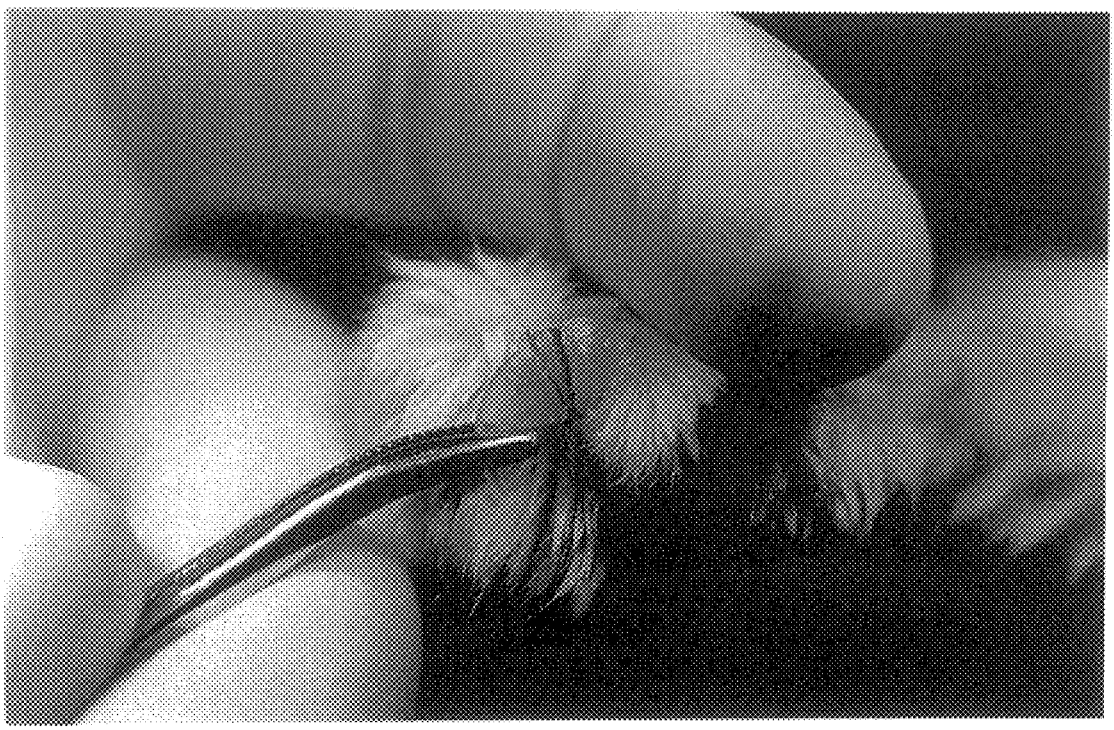
FIG. 13 is a photographic illustration of the claw after the second circumferential incision in the epidermis about 3 millimeters cranial to the first circumferential incision.
Figure 14:
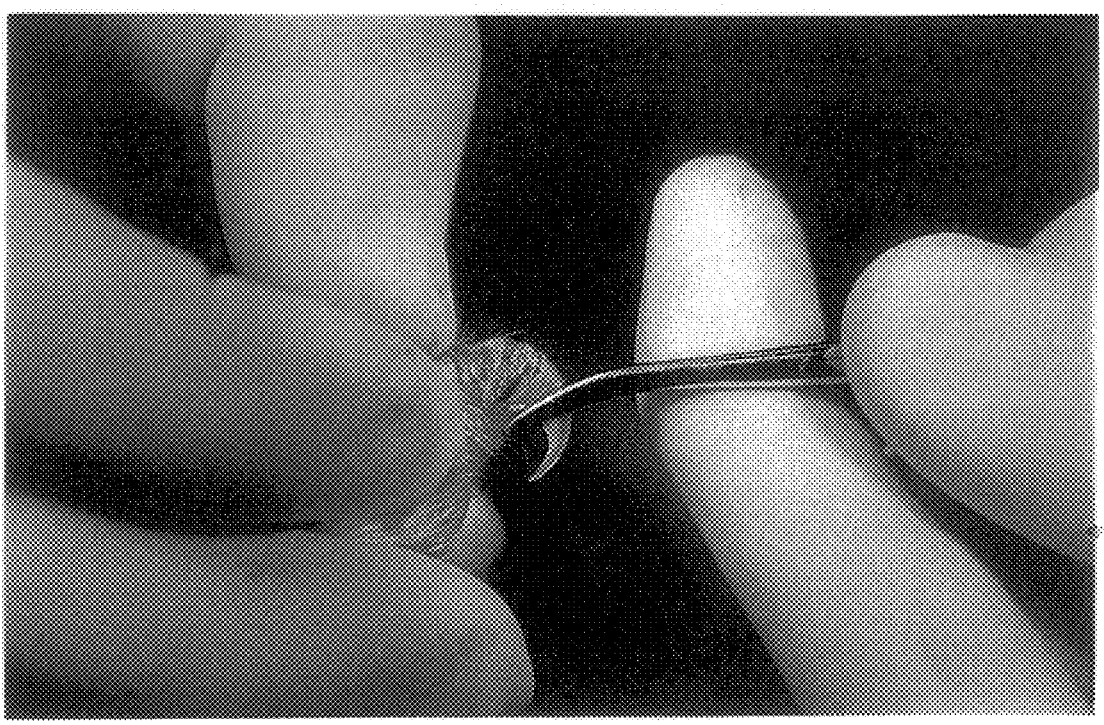
FIG. 14 is a photographic illustration of the claw after the second circumferential incision in the epidermis about 3 millimeters cranial to the first circumferential incision. The redundant epidermis is pushed cranially to the incisions.
Figure 15:
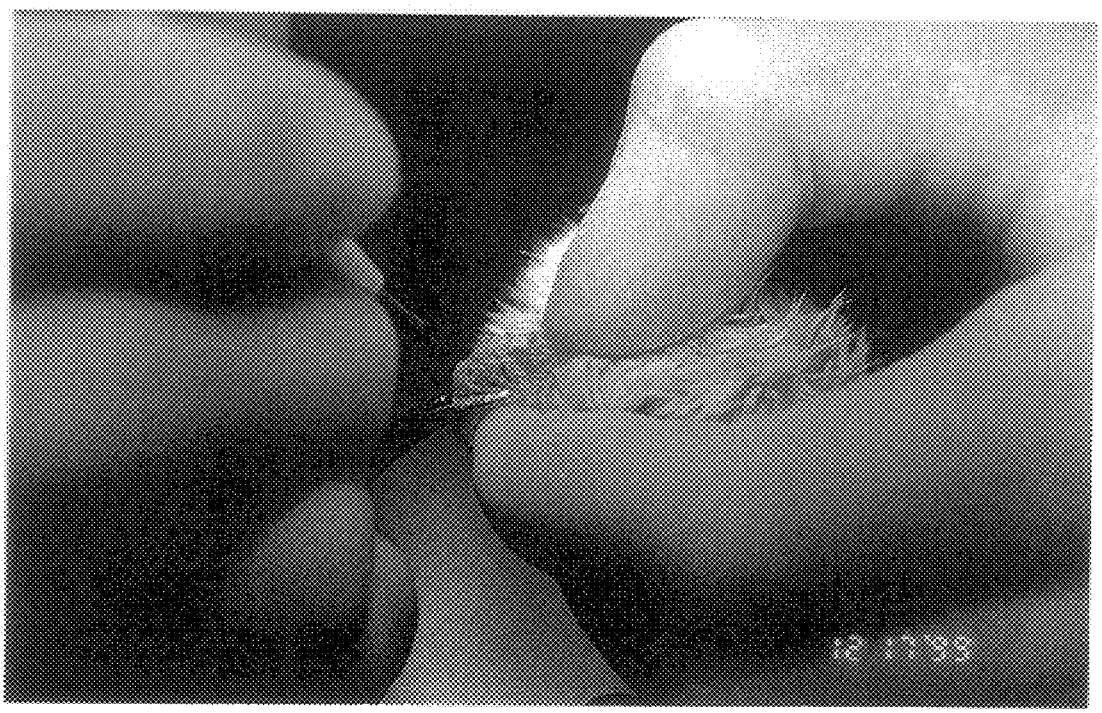
FIG. 15 is a photographic illustration of the claw after the second circumferential incision in the epidermis about 3 millimeters cranial to the first circumferential incision. The extensor ten don is exposed.
Figure 16:
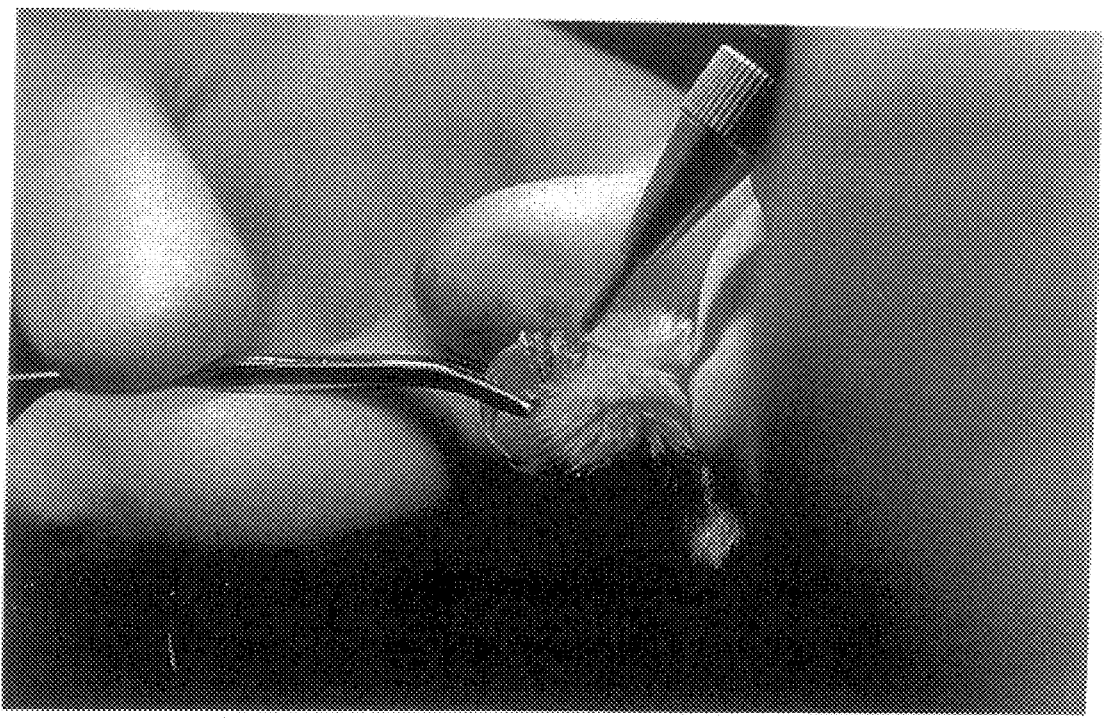
FIG. 16 is a photographic illustration of the incision of the extensor tendon.
Figure 17:
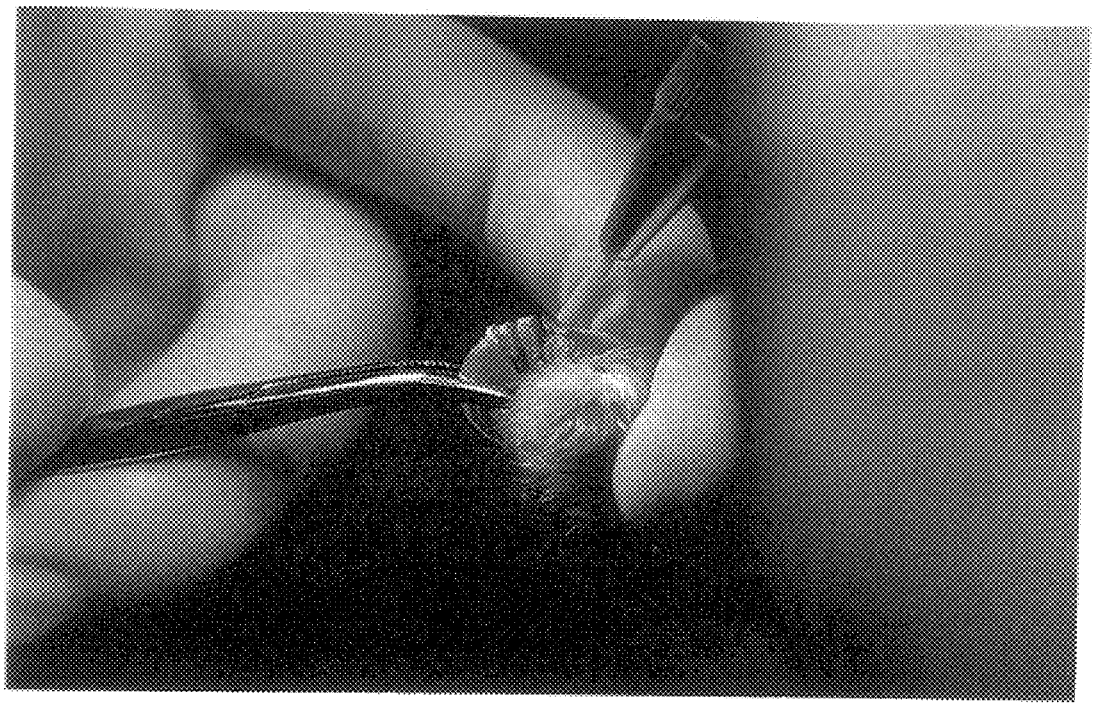
FIG. 17 is a photographic illustration of the synovium of the PII–PIII joint.
Figure 18:
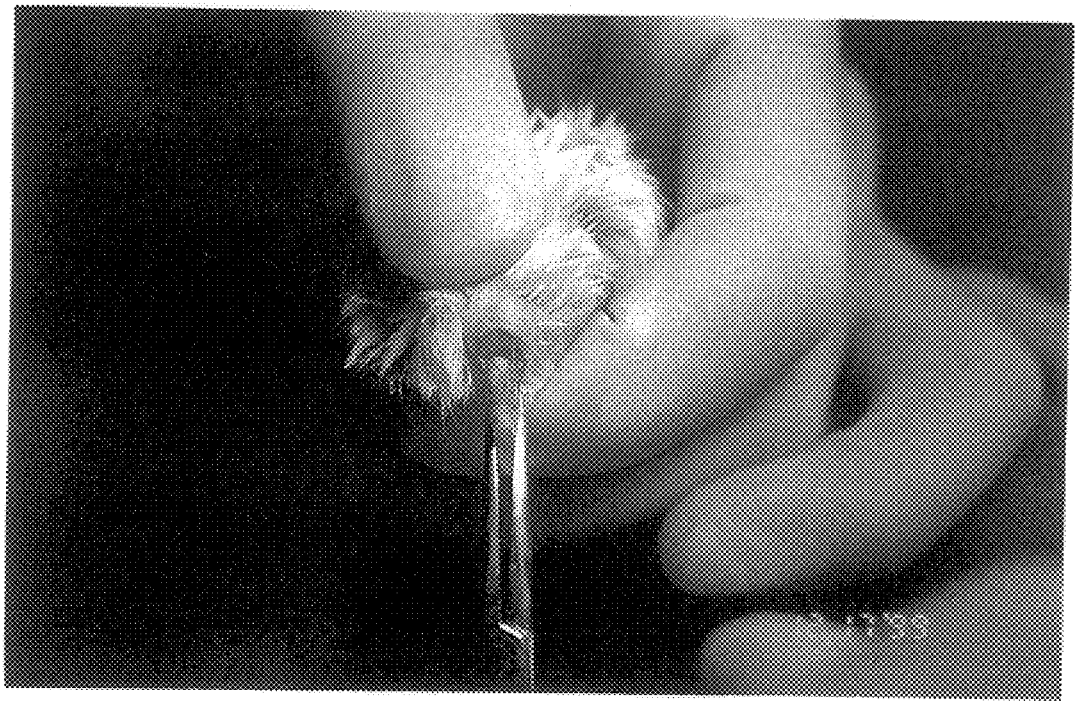
FIG. 18 is a photographic illustration of the medial and lateral collateral ligaments.
Figure 19:
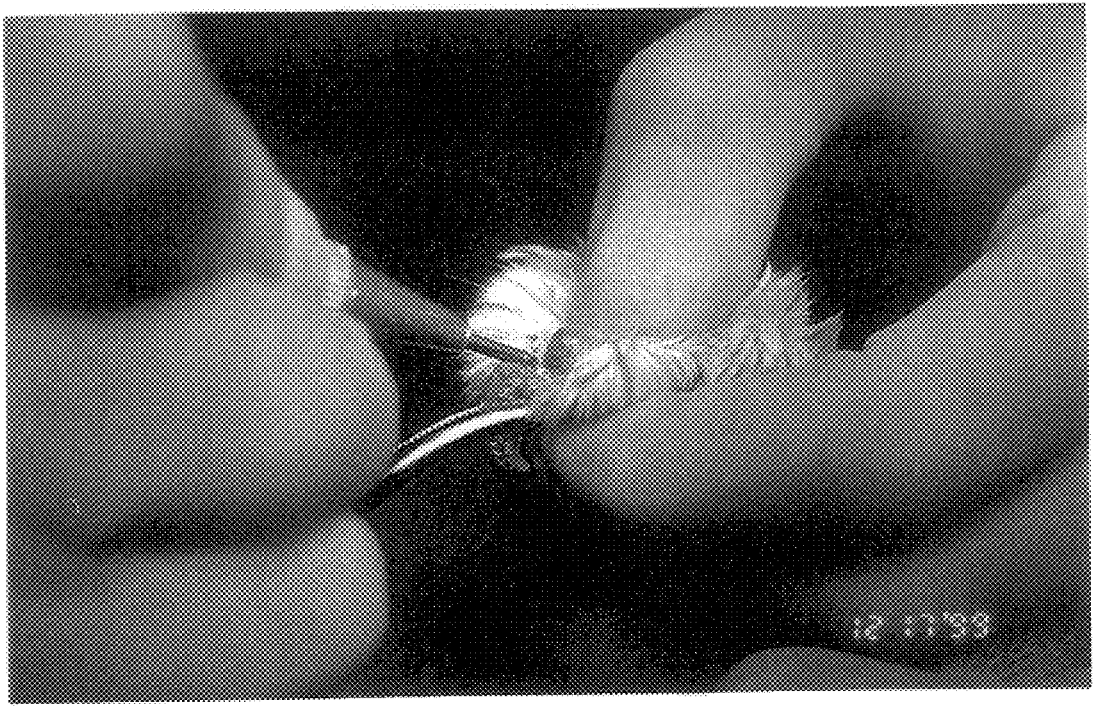
FIG. 19 is a photographic illustration of the plane of incisions of the medial and lateral collateral ligaments.
Figure 20:
FIG. 20 is a photographic illustration of the incising of the digital flexor tendon.
Figure 21:
FIG. 21 is a photographic illustration of the extreme disarticulation of the PII–PIII joint prior to incising the subcutaneous tissues of the pad.
Figure 22:
FIG. 22 is a photographic illustration of the incising of the subcutaneous tissues of the pad of the second phalanx.
Figure 23:
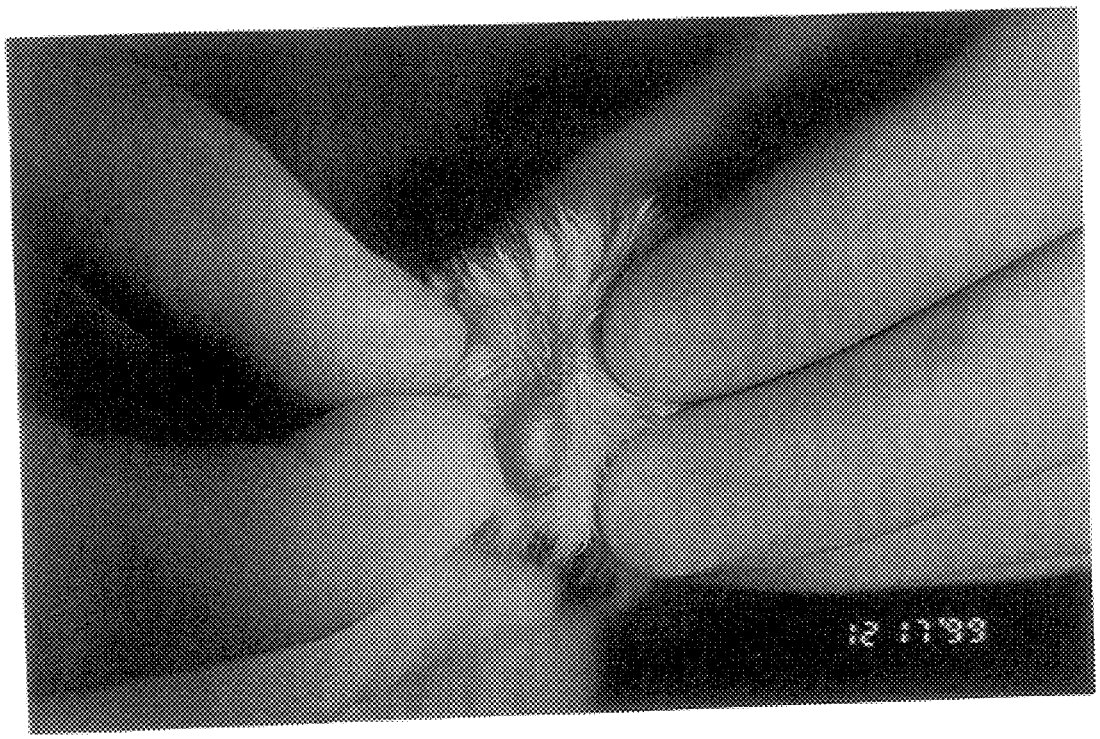
FIG. 23 is a photographic illustration of the declaw site with the redundant epithelium covering the onychectomy site.
Figure 24:
FIG. 24 is a photographic illustration of the declaw site with the redundant epithelium covering the onychectomy site.

Once the claw or claws have been removed, the surgeon should inspect the site and clean it as necessary. The redundant epithelium is then pushed over the declaw site to cover and protect it as shown in FIG. 7. After the site is healed, the epithelium that was preserved during surgery provides a significantly improved declaw site over those that remain after conventional onychectomy procedures.

While certain preferred embodiments of the present invention have been disclosed in detail, it is to be understood that various modifications may be adopted without departing from the spirit of the invention or scope of the following claims.

What is claimed is:

1. A feline onychectomy surgical method using a laser cutting instrument, the method comprising:
   (a) forming a first circumferential incision in the epidermis near the edge of the ungual crest of the claw, thereby severing at least some of the epidermis from the ungual crest;
   (b) applying cranial traction to the epidermis severed from the ungual crest to displace the distal edge of the epithelium cranially;
   (c) incising the extensor tendon near its insertion on the ungual crest;
   (d) incising the synovium of the PII–PIII joint;
   (e) applying traction to the claw in the palmar direction for disarticulating the PII–PIII joint;
   (f) ablating the medial and lateral collateral ligaments;
   (g) incising the digital flexor tendon; and
   (h) incising the subcutaneous tissues of the pad of the second phalanx.

2. The surgical method in accordance with claim 1, wherein the steps of incising and ablating further comprise directing the laser beam in a substantially palmar direction from a laser beam source positioned substantially dorsally of the tissue being incised.

3. The surgical method in accordance with claim 2, further comprising forming a second circumferential incision in the epidermis cranial to the first circumferential incision, thereby severing at least some of the subcutaneous fascia from the ungual crest.

4. The surgical method in accordance with claim 3, wherein the second circumferential incision is formed about three millimeters cranial to the first circumferential incision.

5. The surgical method in accordance with claim 4, further comprising applying cranial traction to the epidermis severed from the ungual crest for covering the onychectomy site.

6. A feline onychectomy surgical method using a laser cutting instrument, the method comprising:
   (a) forming a first circumferential incision with the laser in the epidermis at the edge of the ungual crest of the feline's claw, thereby severing at least some of the epidermis from the ungual crest; and then
   (b) applying cranial traction to the epidermis severed from the ungual crest to displace the distal edge of the epidermis cranially; and then
   (c) forming a second circumferential incision in the epidermis about 3 millimeters cranial to the first circumferential incision, thereby severing at least some of the subcutaneous fascia from the ungual crest; and then
   (d) incising the extensor tendon near its insertion on the ungual crest by directing the laser beam in a substantially palmar direction from a laser beam source positioned substantially dorsally of the extensor tendon; and then
   (e) incising the synovium of the PII–PIII joint; and then
   (f) applying traction to the claw in the palmar direction for disarticulating the PII–PIII joint; and then
   (g) ablating the medial and lateral collateral ligaments by directing the laser beam in a substantially palmar direction from the source positioned substantially dorsally of the ligaments; and then
   (h) incising the digital flexor tendon by directing the laser beam in a substantially palmar direction from the source positioned substantially dorsally of the flexor tendon; and then
   (i) incising the subcutaneous tissues of the pad of the second phalanx by directing the laser beam in a substantially palmar direction from the source positioned substantially dorsally of the subcutaneous tissues of the pad of the second phalanx; and then
   (j) applying palmar traction to the epidermis severed from the ungual crest for covering the onychectomy site.

* * * * *

EX PARTE REEXAMINATION CERTIFICATE (5731st)
United States Patent
Young

(10) Number: US 6,502,579 C1
(45) Certificate Issued: Mar. 27, 2007

(54) LASER ONYCHECTOMY BY RESECTION OF THE REDUNDANT EPITHELIUM OF THE UNGUAL CREST

(76) Inventor: William P. Young, 5860 Waterloo Rd., Canal Winchester, OH (US) 43110

Reexamination Request:
No. 90/007,105, Jun. 30, 2004

Reexamination Certificate for:
Patent No.: 6,502,579
Issued: Jan. 7, 2003
Appl. No.: 09/761,993
Filed: Jan. 17, 2001

Related U.S. Application Data

(60) Provisional application No. 60/176,965, filed on Jan. 19, 2000.

(51) Int. Cl.
*A61B 19/00* (2006.01)
*A61B 18/18* (2006.01)
*A61B 17/22* (2006.01)
*B66F 15/00* (2006.01)
*B25C 11/00* (2006.01)

(52) U.S. Cl. .......................... 128/898; 606/9; 606/127; 254/18

(58) Field of Classification Search .................. None
See application file for complete search history.

(56) References Cited

PUBLICATIONS

Howard E Evans; Miller's Guide to the Dissection of the Dog; book; 1980; pp. 17, 36, and 43; Second Edition; W. B. Saunders Company; Philadelphia, PA.

Howard E Evans; Miller's Anatomy of the Dog; book; 1993; pp. 195–197; Third Edition; W. B. Saunders Company; Philadelphia PA.

Oskar Schaller; Illustrated Veterinary Anatomical Nomenclature; book; 1992; pp. 60–61; Druckhaus Gotz KG; Ludwigsburg, Germany.

M. J. Shively; Veterinary Anatomy; book; 1984; p. 548; Texas A&M University Press; College Station, TX.

Jon Geller, DVM; Doing it Right: Feline Onychectomy; Veterinary Technician journal; Oct. 1999; pp. 549–553; vol. 20, No. 10; publisher unknown.

Mark C Rochat; Amputation of the Digit; manual; 2006; pp. 1167–1169 and 1171; Third Edition; Saunders Elsevier; St. Louis, MO.

Chris Pasquini; Anatomy of Domestic Animals; book; 1995; p. 110; 7th Edition; Sudz Publishing; Pilot Point, TX.

Murray E Fowler; Zoo & Wild Animal Medicine; book; 1986; p. 552; Second Edition; W. B. Saunders Company; Philadelphia, PA.

Douglas H Slatter; Textbook of Small Animal Surgery; book; 1985; pp. 509–510; vol. I; W. B. Saunders Company; Philadelphia PA.

Hudson/Hamilton; Atlas of Feline Anatomy for Veterinarians; book; 1993; pp. 66–67; W. B. Saunders Company; Philadelphia PA.

Douglas Slatter; Textbook of Small Animal Surgery; book; 1993; pp. 352–354; Second Edition, vol. 1; W. B. Saunders Company; Philadelphia, PA.

Theresa Welch Fossum; Small Animal Surgery; book; 1997; pp. 145–147; Mosby, Inc.; St. Louis, MO.

(Continued)

*Primary Examiner*—Beverly M. Flanagan

(57) ABSTRACT

A surgical process for removing the third phalanx of a feline, and most commonly a housecat, while reducing bleeding, swelling, pain and tissue deficit. A circumferential incision is formed on the epidermis of the ungual crest and traction is applied to the epidermis in a cranial direction. This exposes the extensor tendon and synovium, which are incised by the laser from a dorsal position aimed in a palmar direction. While applying traction to the third phalanx in a palmar direction, the collateral ligaments are ablated, permitting further disarticulation of the PII-PIII joint. Finally, the flexor tendon and tissue of the pad are incised by the laser from a dorsal position, permitting removal of the third phalanx. The declaw site is then covered with the redundant epithelium preserved in this process.

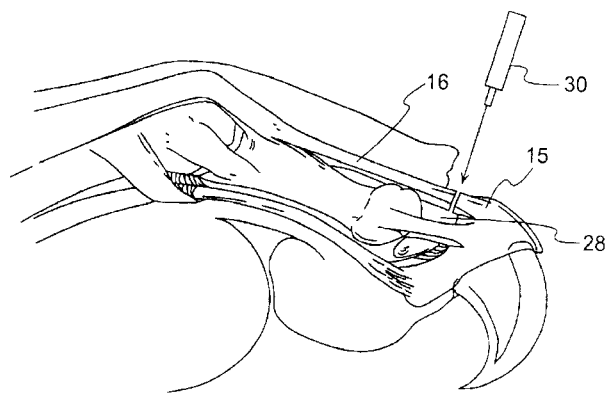

OTHER PUBLICATIONS

Theresa Welch Fossum; Small Animal Surgery; book; 2002; pp. 202–204; Second Edition; Mosby, Inc.; St. Louis, MO.

Andrew Jendrek, D.V.M.; Hottest Technique For Declaws; Veterinary Forum; Forum Letters; Oct. 1999; p. 28; publisher unknown.

Jon Geller, D.V.M.; Doing It Right: Feline Onychectomy; Veterinaryn Technician; Peer–Reviewed CE Article #1; Oct. 1999; vol. 20., No. 10; pp. 549–553; publisher unknown.

Rick Wall, D.V.M.; CO2 Laser in Clinical Practice; title of item unknown; date, page number and publisher unknown.

Author unknown; Vet uses Lasers to Reduce Discomfort; Server & Eccentric; May 21, 1998; page and publisher unknown.

John Finnerty; Vets are First in State with Laser Treatment; Western Sussex Snippet; date unknown; pp. 1 and 2; publisher unknown.

Author unknown; Local Vet Beaming Pets to Better Health; Mandarin News & St. Johns River; Sep. 24, 1998; Section 2; publisher unknown.

Sarah Casey Newman; The Tail End—Laser Surgery for Animals is Called a Howling Success; St. Louis Post Dispatch; Apr. 10, 1999; Page and publisher unknown.

Author unknown; Laser Surgery Cuts Pets' Pain, Recovery Time; Morning News, Erie, PA; Sep. 24, 1998; p. 7B; publisher unknown.

Author unknown; Veterinarians Enter the Laser Age; The Tennessean Williamson A.M.; May 3, 1999; page and publisher unknown.

Stephanie L. Arnold; It's Surgery with Barely a Meow; The Philadelphia Inquirer; date, page and publisher unknown.

Christine Gioannetti; Laser Surgery Available at Clinic; title of item, date, page and publisher unknown.

Ru Schmitt; Pets: On the Cutting Edge; Potomac News; Jun. 2, 1999; page and publisher unknown.

Bonnie Burch; Veterinarians Enter the Laser Age; title of item, date, page and publisher unknown.

Alison Netsel; Let There be Light; Cats & Kittens publication; Jul. 1996;p. 53; publisher unknown.

Elaine Wexler–Mitchell, D.V.M.; Cutting–edge Technology; Cat Fancy publication; Apr. 1998; p. 43; publisher unknown.

Michael Drakulich; High–tech Vet—Animals Now Benefit from Laser Surgery; title of item, date, page and publisher unknown.

Kathy Drasky; Laser Declawing Procedure Offers Viable Alternative to Traditional Surgery; Veterinary Product News; Nov. 1997; page and publisher unknown.

Author unknown; Veterinarians Start Laser Society; Medical Laser Report; Jul. 1999; p. 2; publisher unknown.

Author unknown; Laser Surgery Improves Veterinary Surgical Care; Medco Forum; Jan. 1998; vol. 5; No. 1; publisher unknown.

Charles Hickey, D.V.M.; Declawing Has New Assistance; Letter to the Editor; Veterinary Forum 10; Jan. 1999; page and publisher unknown.

Bob Levoy; How to Achieve a Competitive Edge; Practice Tips—Veterinary Economics; Aug. 1999; p. 17; publisher unknown.

Dr. Michael J. Herman; Local Vet Offers New Laser Declaw Procedure; News Release; May 24; 1999; page and publisher unknown.

Kimberly Herbert; Laser Surgery—Waves of the Future; The Horse publication; Sep. 1995; (6 pages) page and publisher unknown.

Kathy Lu; Maiking Life Easier for Animals—Laser Surgery for Pets Comes to Southwest Virginia; Roanoke Times; Oct. 14, 1997; page and publisher unknown.

Susan Smith; Pioneering Veterinarian Uses Lasers for Surgery, Declawing; title of item, date, page and publisher unknown.

Author unknown; article from The Chesapeake Clipper, Business Section, showing Dr. Rod Hartwick using a laser.

J. Irwin, D.V.M.; 4–Cut Technique for Laser Declaw; title of item, date, page and publisher unknown.

Author unknown; Laser Surgery Improves Veterinary Surgical Care; Medco Forum; Jan. 1998; vol. 5, No. 1; published by Medco Communications Company, Norwalk, CT.

Betsy Powell Mullen; Cutting Edge; Richmond Times Dispatch; Nov. 22, 1997; pp. E1 and E5; publisher unknown.

Alison Netsel; Let There be Light—Lasers Expedite Declawing; Cats & Kittens publication; July 1998; cover and pp. 53 and 54; publisher unknown.

Mary Carter; Star Wars Medicine: Laser Surgery Available for Florida's Pets; The Pet Tribune publication; Oct./Nov. 1998; cover and pp. 13 and 46; publisher unknown.

Solveig Frederickson; Scratching—Understand Why Your Cat Exercises its Claws before Deciding How to Save Your Furniture; Cat Fancy; Feb. 1999; cover and pp. 20–27; publisher unknown.

Fossum, *Small Animal Surgery*, pp. 145–147 (Mosby 1997).

Case 1, *Luxar AccuVet™ Clinical Atlas of Veterinary Procedures* (1998).

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–6 is confirmed.

* * * * *